US010507051B2

(12) United States Patent
Huang et al.

(10) Patent No.: US 10,507,051 B2
(45) Date of Patent: Dec. 17, 2019

(54) X-RAY DETECTABLE BIOABSORBABLE BONE SCREW (71) Applicant: MEDALL BIOTECH CO., LTD., Taipei (TW)

(72) Inventors: Haw-Ming Huang, Taipei (TW); Jy-Jiunn Tzeng, Taipei (TW); Chi-Hsien She, Taipei (TW); Yu-Ming Hsu, Taipei (TW)

(73) Assignee: MEDALL BIOTECH CO., LTD., Taipei (TW)

( * ) Notice: Subject to any disclaimer, the term of this patent is extended or adjusted under 35 U.S.C. 154(b) by 409 days.

(21) Appl. No.: 15/227,810

(22) Filed: Aug. 3, 2016

(65) Prior Publication Data

US 2017/0296246 A1 Oct. 19, 2017

(30) Foreign Application Priority Data

Apr. 13, 2016 (TW) .............................. 105111555 A (51) Int. Cl.
*A61B 17/86* (2006.01)
*A61B 17/00* (2006.01)
(52) U.S. Cl.
CPC ............ *A61B 17/866* (2013.01); *A61B 17/86* (2013.01); *A61B 2017/00526* (2013.01); *A61B 2017/00964* (2013.01)
(58) Field of Classification Search
CPC .............................. A61B 17/866; A61B 17/86
See application file for complete search history.

(56) References Cited

U.S. PATENT DOCUMENTS

| 2003/0065332 A1* | 4/2003 | TenHuisen | A61B 17/8685 606/312 |
|---|---|---|---|
| 2017/0181785 A1* | 6/2017 | Beyar | A61B 17/866 |
| 2018/0140702 A1* | 5/2018 | Guo | C07K 16/00 |

FOREIGN PATENT DOCUMENTS

| CN | 103360607 A | 10/2013 |
|---|---|---|
| CN | 103745793 A | 4/2014 |
| CN | 103360607 B | 1/2016 |

\* cited by examiner

*Primary Examiner* — David W Bates
(74) *Attorney, Agent, or Firm* — Maschoff Brennan (57) ABSTRACT

A X-ray detectable bioabsorbable bone screw comprises a light-emitting element, a light-sensing element, a transparent inner encapsulant body, an outer covering body, and two conductive frames on which. An optically reflective surface is in contact and formed between the dome enclosing portion of the transparent inner encapsulant body and the outer encapsulant body. A portion of the light emitted by the light-emitting element is reflected to the light-sensing element through the optically reflective surface, and the other portion of the light emitted from the light-emitting element is directly emitting to the light-sensing element through the transparent inner encapsulant body. The present invention applies the optically reflective surface to minimize the overlapping area between the two conductive frames, and reduces the capacitance value, and increases the CMRR in a manner that the photo coupler of the present invention is able to meet the standard of electrical characteristics as required.

8 Claims, 8 Drawing Sheets

X-RAY DETECTABLE BIOABSORBABLE BONE SCREW

FIELD OF THE INVENTION

The present invention relates to an X-ray detectable bioabsorbable bone screw, and more particularly to a bone screw, which is radiographable under X-ray exposure and is biocompatible with and biodegradable by the animal cell, where the bone screw can be manufactured by an injection molding process or a 3D printing process.

BACKGROUND OF THE INVENTION

Polylactic acid (PLA) is a thermoplastic polyester material. PLA is biodegradable in human body and can be naturally excreted from the body after being decomposing into $CO_2$ and $H_2O$. In the medical field, PLA has been used to manufacture medical material such as bone screws, bone plates, vascular stents, surgical sutures, surgical guides, drug delivery materials, artificial skin, and wound dressings for medical purposes. These bone screws can be directly implanted into human body to treat bone diseases, where it can be naturally degraded in human body, thereby sparing the necessity of second surgery for removing the bone screws.

Micron-sized ferroferric oxide particles are material with ferrimagnetic properties. While ferroferric oxide particles become smaller than 50 nanometer, they have superparamagnetic properties. This unique property enables nano-sized ferroferric oxide to be well applicable in the biomedical field and the biological engineering field as well. The applicable fields include magnetic bead separation technology, hyperthermia, drug delivery systems, and magnetic resonance imaging (MRI) contrast agents. In addition, a nano-sized ferroferric oxide particles exhibit osteogenic property.

The use of PLA in the manufacture of bone screws is conventional technology, wherein the manufacturing method is achieved by heating PLA to 180 to 198 degrees and then injecting the PLA into a bone screw mold to make the PLA form a bone screw. A Bone screw made of pure PLA is not radiographable under X-ray exposure due to its low mass density and low electron density, and thus it is hard to perform surgical positioning and the evaluation of post-operative degradation when bone screws made of pure PLA are used in surgery. In order to overcome the drawback, some additives such as barium sulfate and bismuth bromide are added into high molecular polymer to overcome the low radiographable property. However, because of the poor biocompatibility that these additives possess, they can cause harmful side effects in human body since the added additives will be released after the high molecular polymer of biodegrade.

Examples of binding high molecular weight polylactic acid to ferroferric oxide nanoparticles can be found in a Chinese utility model patent with publication number CN 103360607A and CN 103360607B, which disclose a method for the preparation of magnetically-responsive star-shaped block copolymer nanomicelle, comprising: using an magnetic iron oxide ($Fe_3O_4$-OH) nanoparticles modified by γ-glycidoxypropyltrimethoxysilane (KH-560) as a nucleation initiator, triggering lactide (LA) to perform active ring opening polymerization by using hydroxyl groups on the surfaces of magnetic nanoparticles and then obtaining a magnetic star-shaped polymer as a nucleus, and esterifing the star-shaped polymer with carboxylated methoxy-polyethylene glycol(CMPEG) to synthesize a magnetically-responsive star-shaped block copolymer nanomicelle. The purpose thereof is to prepare a magnetic high molecular weight polymer material. In addition, another example of binding high molecular weight polylactic acid to iron oxide nanoparticles can be found in Chinese utility model patent with publication number CN 103745793 A, which discloses a method for the preparation of a targeted superparamagnetic liposome-polylactic acid (PLA) nanoparticles and method for the preparation thereof, comprising: forming PLA-phospholipid-PEG nanoparticle by coating polylactide on $Fe_3O_4$ as a PLA core, coating a single layer of phospholipid on the surface of the PLA core, and alternately adding distearoyl phosphatidyl ethanolamine-polyethylene glycol-carboxylic acid in the single layer of phospholipid. The purpose thereof is to develop a magnetically adsorptive material for separating tumor cells. However, these preparation methods cannot be applied to the preparation of a bioabsorbable PLA bone screw which is radiographable under X-ray exposure.

Therefore, it is the object of the present invention to provide a bone screw which is radiographable under X-ray exposure so as to overcome the problem of the conventional bone screws which is radiopaque. The present invention is also with advantage of being bioabsorbable such that the bone screw, while being radiographable, can still be degraded in human body in such a manner that it can spare the necessity of second surgery for removing the bone screws.

SUMMARY OF THE INVENTION

In view of the above circumstances, an object of the present invention is to provide an X-ray detectable bioabsorbable bone screw, which is radiographable under X-ray exposure, comprising: a screw member having a cylindrical shape; and a cap member provided on an end of the screw member and being extended outwardly from the screw member, wherein the cap member and the screw member are formed integrally, and the cap member and the screw member are made of polylactic acid and iron oxide nanoparticles.

According to a preferred embodiment of the present invention, the cap member and the screw member contain 0.5 to 40 weight percent of iron oxide nanoparticles.

According to a preferred embodiment of the present invention, the cap member and the screw member are manufactured by an injection molding process or a 3D printing process.

According to a preferred embodiment of the present invention, a length extending in an axial direction of the x-ray detectable bioabsorbable bone screw is 16 mm and a diameter of the screw member is 3.1 mm.

According to a preferred embodiment of the present invention, the X-ray detectable bioabsorbable bone screw further comprises a bioabsorbable material, which is selected from a group consisting of hydroxyapatite (HAP), β-tricalcium phosphate (β-TCP) and calcium polyphosphate (CPP).

According to a preferred embodiment of the present invention, the X-ray detectable bioabsorbable bone screw is biocompatible with an animal cell and is biodegradable by the animal cell.

According to a preferred embodiment of the present invention, the X-ray detectable bioabsorbable bone screw is manufactured by an injection molding process.

According to a preferred embodiment of the present invention, the X-ray detectable bioabsorbable bone screw is manufactured by a die casting process.

According to a preferred embodiment of the present invention, the X-ray detectable bioabsorbable bone screw is manufactured by a 3D printing process.

BRIEF DESCRIPTION OF THE DRAWINGS

The structure and the technical means adopted by the present invention to achieve the above and other objects can be best understood by referring to the following detailed description of the preferred embodiments and the accompanying drawings.

DETAILED DESCRIPTION OF THE PREFERRED EMBODIMENTS

Figure 2:
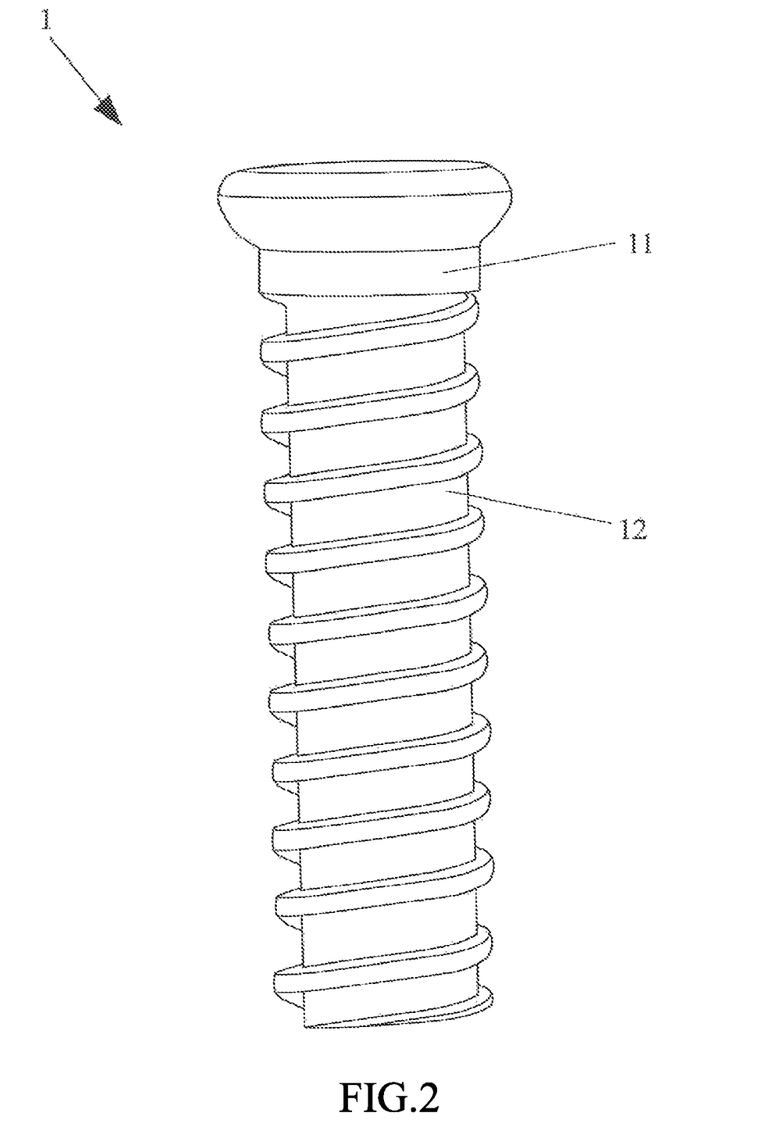
FIG. 2 is a schematic diagram illustrating the X-ray detectable bioabsorbable bone screw.

As illustrated in FIG. 2, an X-ray detectable bioabsorbable bone screw 1 comprises a screw member 12 and a cap member 11. The screw member 12 has a cylindrical shape. The cap member 11 is provided on an end of the screw member 12 and extended outwardly from the screw member 12. The cap member 11 and the screw member 12 are formed integrally, and the cap member 11 and the screw member 12 are made of polylactic acid and iron oxide nanoparticles. A nanoparticle is defined as a microscopicparticle with at least one dimension less than 100 nm. Preferably, the sizes of the iron oxide nanoparticles are less than 50 nanometer in size.

Figure 1:
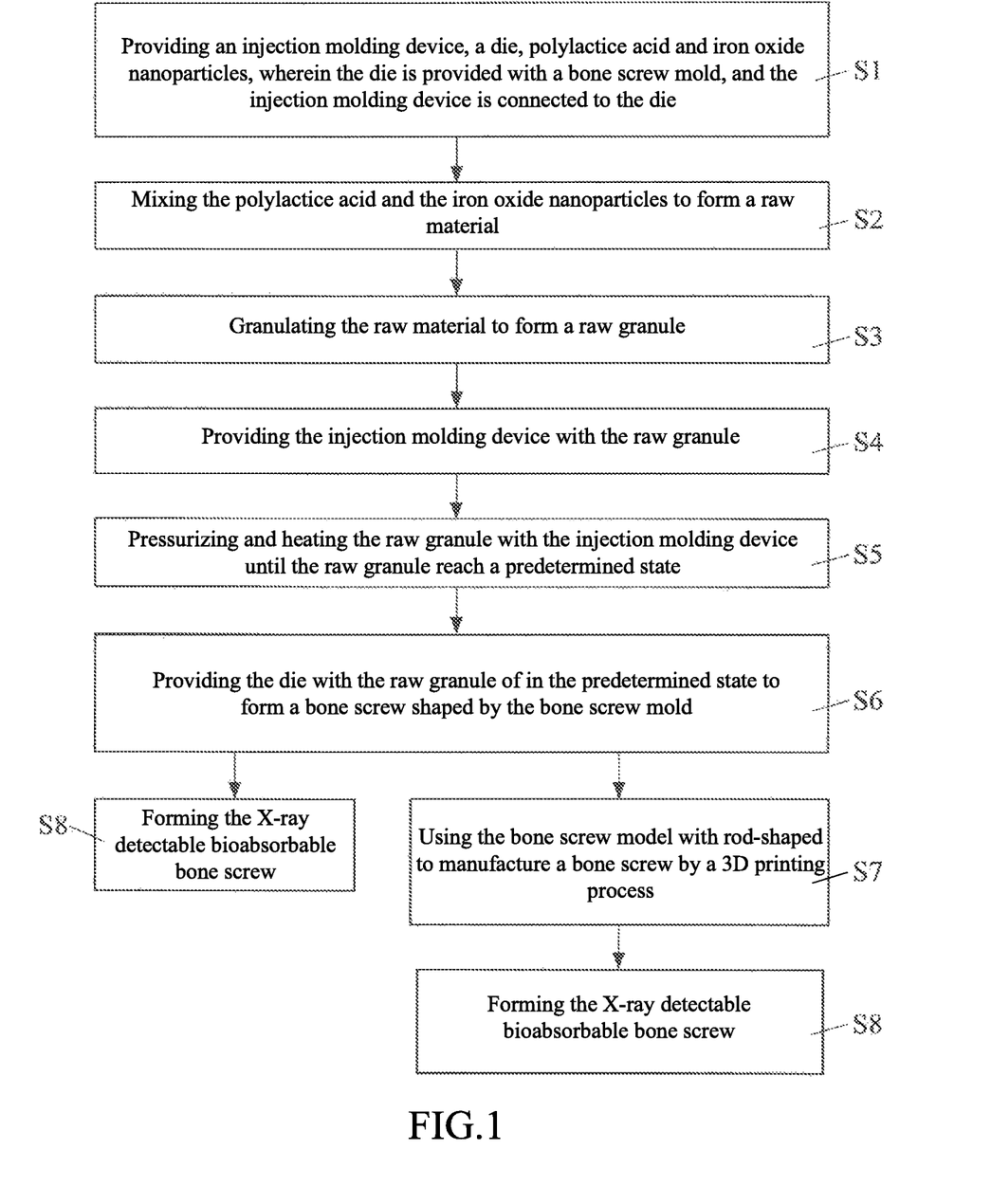
FIG. 1 is a flow diagram illustrating a method of manufacturing an X-ray detectable bioabsorbable bone screw according to an embodiment of the present invention.

As shown in the flow diagram of FIG. 1, the method of manufacturing the X-ray detectable bioabsorbable bone screw is described according to steps S1 to S8. The method of manufacturing the bone screw comprises steps of: providing an injection molding device, a die, polylactic acid and iron oxide nanoparticles, wherein the die is provided with a bone screw mold, and the injection molding device is connected to the die; mixing the polylactic acid and the iron oxide nanoparticles to form a raw material; granulating the raw material to form a raw granule; providing the injection molding device with the raw granule; pressurizing and heating the raw granule with the injection molding device until the raw granule reach a predetermined state; providing the die with the raw granule of in the predetermined state to form a bone screw shaped by the bone screw mold. The embodiment of the present invention will be described in detail with reference to the appended drawings hereinafter in order to make the objects, characteristics and advantages of the present invention more clear and comprehensible.

Preparation Example 1

Figure 3:
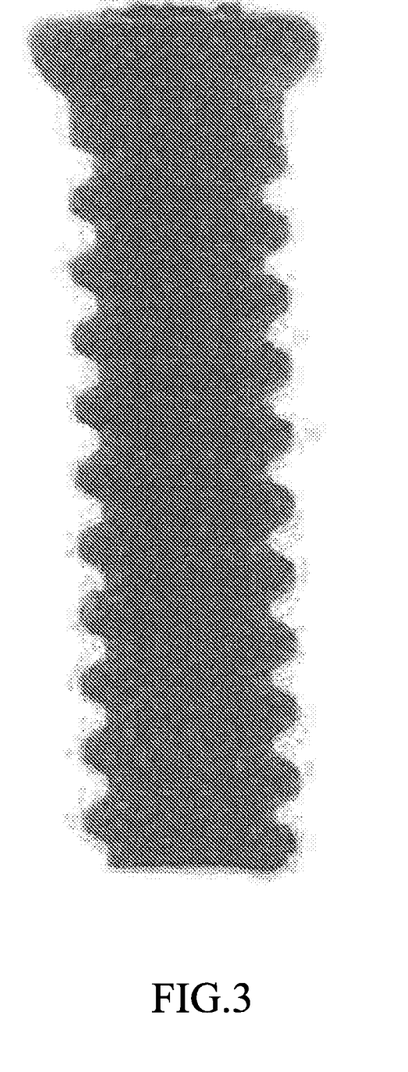
FIG. 3 is a radiograph illustrating the X-ray detectable bioabsorbable bone screw manufactured by an injection molding process.

Injection molding method, a conventional plastic processing method, is employed to manufacture a bone screw model. Pure PLA granules and iron oxide nanoparticles are mixed to form a raw material, and the raw material is granulated to obtain a PLA raw granule containing 20 wt % iron oxide nanoparticles as a raw granule. The raw granule is pressurized and heated by the injection molding device until the raw granule reaches a predetermined state. The die is filled with the raw granule in the predetermined state rapidly, and the pressure is kept constant until the raw material is cooled. After the raw material is cooled, the raw material is demolded to form a bone screw model which is shaped by the bone screw mold. The bone screw model is manufactured by an injection molding process. The bone screw model can be used to make bone screws of specific size. More specifically, the bone screw model can be used to manufacture, by injection molding process, a bone screw with a length of 11-20 mm in an axial direction, and a diameter of 2.5-3.6 mm. In this preparation example, as shown in FIG. 3, the bone screw model is used to manufacture bone screws with a length of 2.5 mm in the axial direction, and a diameter of 3.1 mm. However, the present invention is not limited to this. Furthermore, in order to make the present invention applicable to various parts of the body to be treated and various bone diseases, other bioabsorbable material, such as hydroxyapatite, β-tricalcium phosphate and calcium polyphosphate, is selectively added into the PLA raw material. In addition, PLA can be substituted by materials as follows: polyglycolic acid (PGA), polycaprolactone (PCL), polyethylene glycol (PEG), lactic acid-glycol copolymer, polydioxanone (PDO) and/or chitin. The iron oxide nanoparticles include $Fe_2O_3$, $Fe_3O_4$ and FeO. Iron oxide nanoparticles can be substituted by materials as follows: nano-sized oxides of iron, cobalt, nickel and/or chromium, such as $Fe_2CoO_4$, NiO and $CrO_2$.

Preparation Example 2

Figure 4:
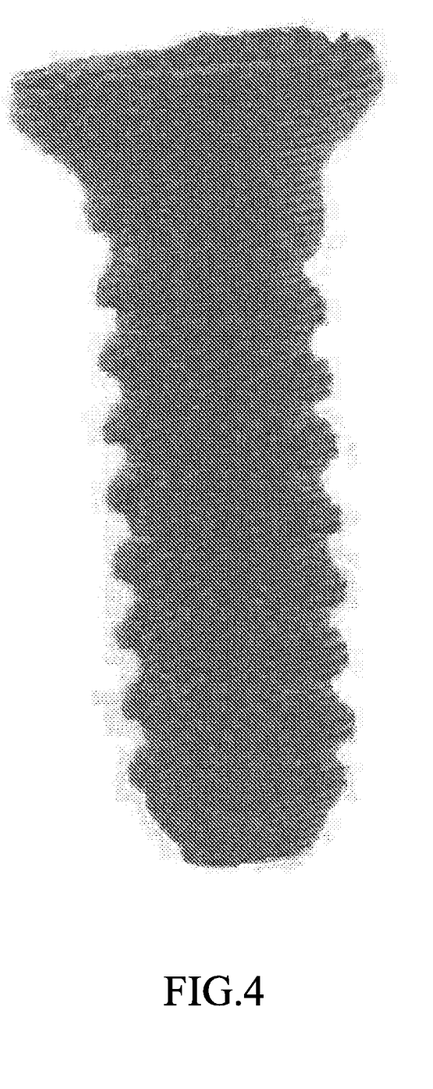
FIG. 4 is a radiograph illustrating the X-ray detectable bioabsorbable bone screw manufactured by a 3D printing process.

Besides the injection molding process, the bone screw can be manufactured by a 3D printing process. The bone screw model is rod-shaped and can be applied to a 3D printing process, in which the bone screw model is used to manufacture a bone screw by a 3D printing process. As mentioned above, pure PLA raw material and iron oxide nanoparticles are mixed to form a raw material, and the raw material is granulated to obtain a PLA raw granule containing 20 wt % iron oxide nanoparticles as a raw granule. The raw granule is pressurized and heated by the injection molding device until the raw granule reaches a predetermined state. The die is filled with the raw granule in the predetermined state rapidly, and the pressure is kept constant until the raw material is cooled. After the raw material is cooled, the raw material is demolded to form a bone screw model with a length in an axial direction of is 20 mm and a diameter of 1.65 mm. The bone screw model, which is rod-shaped, can be applied to an additive manufacturing device. A bone screw of 16 mm in length and 3.1 mm is formed by utilizing 3D printing process (as shown in FIG. 4) with the bone screw model being used as a 3D printing model. Furthermore, in order to make the present invention applicable to various parts of the body to be treated and various bone diseases, other bioabsorbable material, such as hydroxyapatite, β-tricalcium phosphate and calcium polyphosphate, is selectively added into the PLA raw material. In addition, PLA can be substituted by materials as follows: polyglycolic acid (PGA), polycaprolactone (PCL), polyethylene glycol (PEG), lactic acid-glycol copolymer, polydioxanone (PDO) and/or chitin. The iron oxide nanoparticles include $Fe_2O_3$, $Fe_3O_4$ and FeO. Iron oxide nanoparticles can be substituted by materials as follows: nano-sized oxides of iron, cobalt, nickel and/or chromium, such as $Fe_2CoO_4$, NiO and $CrO_2$.

Preparation Example 3

In order to prove that the cap member 11 and the screw member 12 containing 0.5 to 40 weight percent of iron oxide nanoparticles is able to be manufactured and is radiographable under X-ray exposure, polylactic acid and iron oxide nanoparticles are mixed in different mix proportions by weight, producing Fe3O4/PLA samples at different weight ratios: 0 wt %, 20 wt %, 30 wt % and 40 wt %. A plurality of I-shaped specimens for tensile strength testing are manufactured with the Fe3O4/PLA samples by an injection molding process according to the ASTM (American Society for Testing and Materials) D638 Type V testing standard. The I-shaped specimens have the following specifications: a width of 2.6 mm, a thickness of 4.2 mm and a parallel length of 20 mm. During the tensile strength testing, the I-shaped specimens manufactured by the injection molding process are provided on a clamping member of the tensile strength testing device, and a set the strain rate to be 2 mm/min to measure and record the yield strength of the I-shaped specimens. The yield strength of the I-shaped specimens is shown in Table I.

TABLE I

| Content of iron oxide nanoparticles | 0 wt % | 20 wt % | 30 wt % | 40 wt % |
| --- | --- | --- | --- | --- |
| Yield strength (MPa) | 51.1 | 49.2 | 42.7 | 41.5 |

Embodiment 1

Biocompatibility Testing

The bone screw is immersed in sterile water and oscillated by an ultrasonic oscillator for 10 minutes, and then immersed in 75% alcohol as a cleaning step. The bone screw is sterilized by γ-ray, after which the preoperative preparation for an animal experiment is completed. A New Zealand white rabbit is anesthetized by receiving a subcutaneous cervical injection; an implantation area at the front hind leg of the New Zealand white rabbit was shaved; a position in the implantation area to be cut is locally anesthetized with Lidocaine; subcutaneous layer and muscular layer are cut open with surgical scalpel blades No. 15 from a marked point in the middle of the two joints at both ends of the femur along a front side of the femur in a long axial direction; and the periosteum above the femur is lifted to expose femur. A proximal portion of the femoral diaphysis that is away from the articular pan is determined to be implanted. The bone tissue of the part to be implanted is drilled by a drilling machine and is rinsed with physiological saline, and the physiological saline is extracted. After the drilling is completed, the bone screw is implanted, and the subcutaneous layer and the muscular layer are sutured with 5-0 absorbable suture, and then epidermis is sutured with suture.

The rabbit is sacrificed 4 weeks after the surgery. The femur containing the bone screw is resected and immersed in a fixative solution containing 10% formalin. Then, the femur sample containing the bone screw is dehydrated through multiple processes, and then is wrapped with paraffin and sliced to form a paraffin section. The paraffin section is stained by Hematoxylin-Eosin Staining method and then a section slide of the paraffin section is prepared using mounting media. Then, the femur sample containing the bone screw is scanned by a slice-scanner, and an image file of the section slide obtained therefrom is observed.

Figure 5:
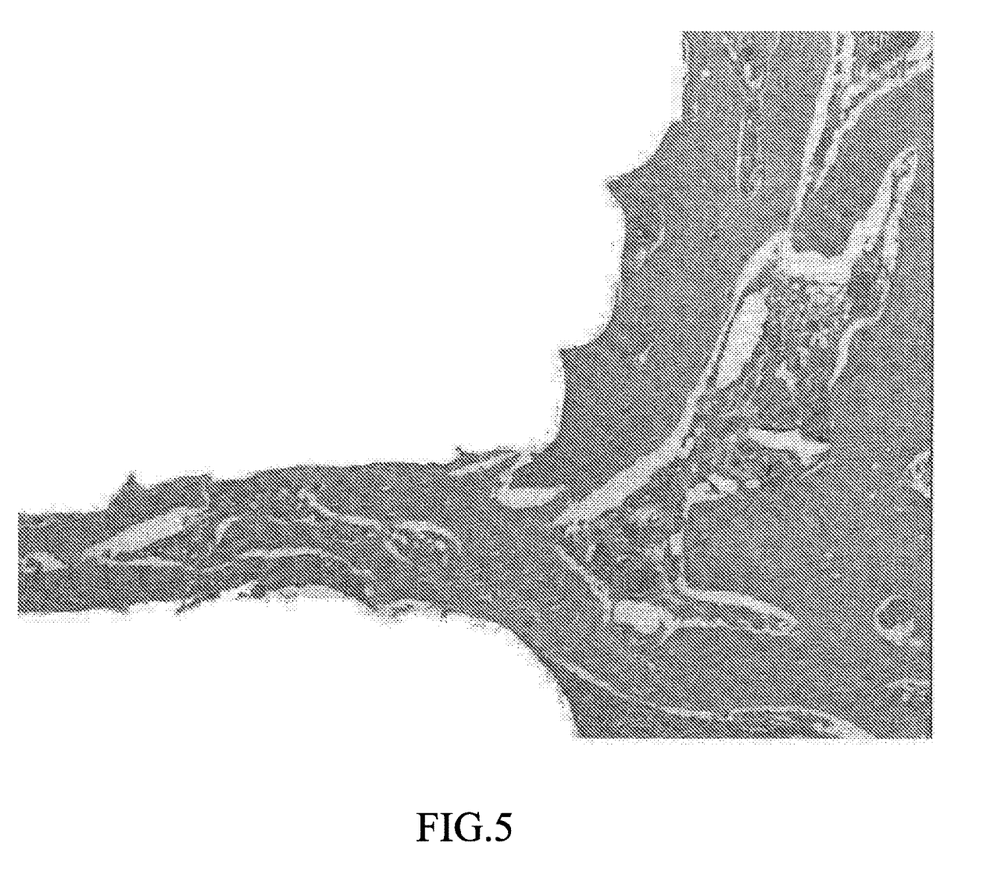
FIG. 5 is a photomicrograph illustrating a degradation condition of the X-ray detectable bioabsorbable bone screw of the present invention implanted in a rabbit bone.

After the bone screw of the present invention is degraded, the substance released from degradation is shown as the black parts in FIG. 5. The substance does not initiate an inflammatory response within body and can be covered by bone tissue, on which bone cells can grow. It is thus indicated that the bone screw of the present invention is biocompatible.

Embodiment 2

Examination of X-Ray Detectability

The bone screw is immersed in sterile water and oscillated by an ultrasonic oscillator for 10 minutes, and then immersed in 75% alcohol as a cleaning step. The bone screw is sterilized by γ-ray, after which the preoperative preparation for an animal experiment is completed. A New Zealand white rabbit is anesthetized by receiving a subcutaneous cervical injection; an implantation area at the front hind leg of the New Zealand white rabbit was shaved; a position in the implantation area to be cut is locally anesthetized with Lidocaine; subcutaneous layer and muscular layer are cut open with surgical scalpel blades No. 15 from a marked point in the middle of the two joints at both ends of the femur along a front side of the femur in a long axial direction; and the periosteum above the femur is lifted to expose femur. A proximal portion of the femoral diaphysis that is away from the articular pan is determined to be implanted. The bone tissue of the part to be implanted is drilled by a drilling machine and is rinsed with physiological saline, and the physiological saline is extracted. After the drilling is completed, the bone screw is implanted, and the subcutaneous layer and the muscular layer are sutured with 5-0 absorbable suture, and then epidermis is sutured with suture.

The rabbit is sacrificed 4 weeks after the surgery. The femur containing the bone screw is resected and immersed in a fixative solution containing 10% formalin. The femur section is scanned by a micro computed tomography (Micro CT) scanner for observation. The parts of the femur sample to be observed, including the bone screw and the bone tissue around the bone screw, are circled using a built-in instructional tool of the micro computed tomography to calculate the volume of new bone.

Figure 6A:
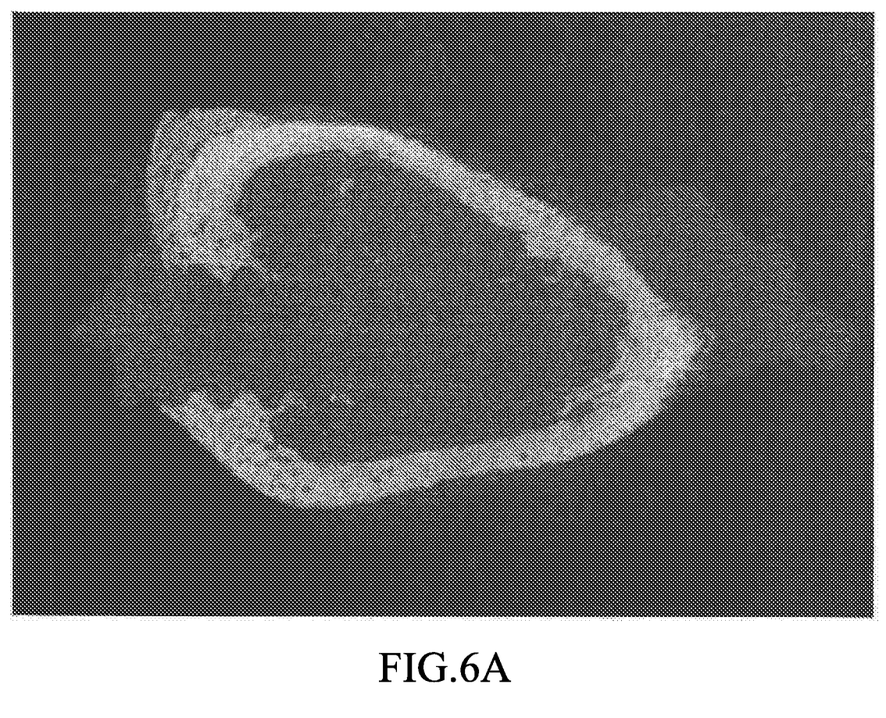
FIG. 6a is a radiograph illustrating that a position of a conventional bone screw made of pure PLA in a bone is unlocatable when being exposed to X-ray radiation.
Figure 6B:
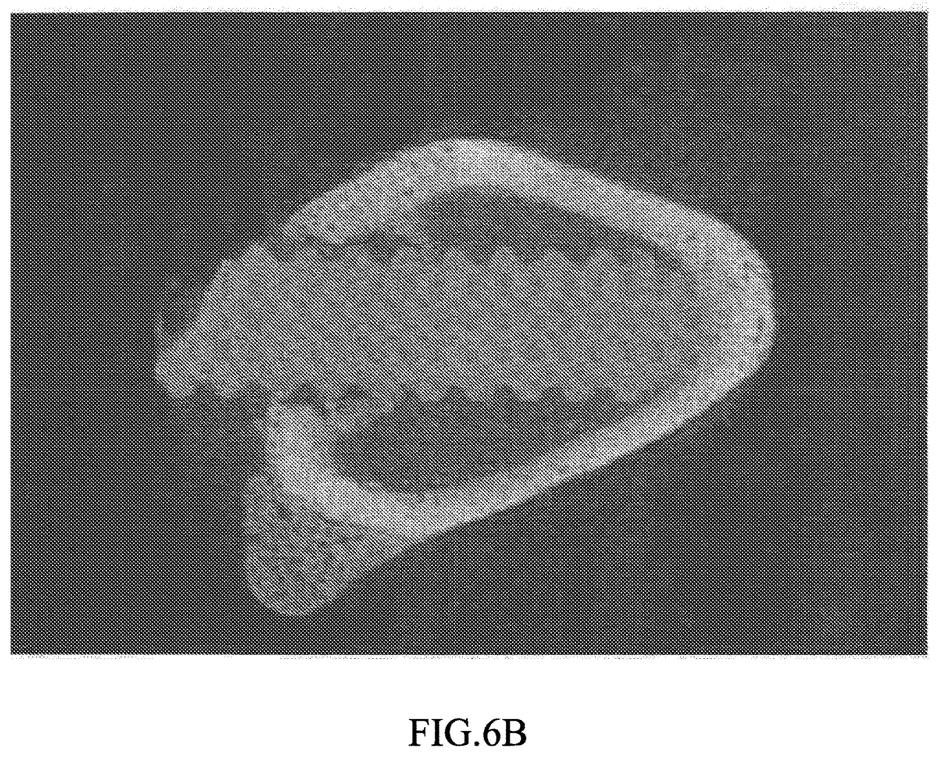
FIG. 6b is a radiograph illustrating that the bone screw of the present invention in a bone is clearly identified when being exposed to X-ray radiation.
Figure 7:
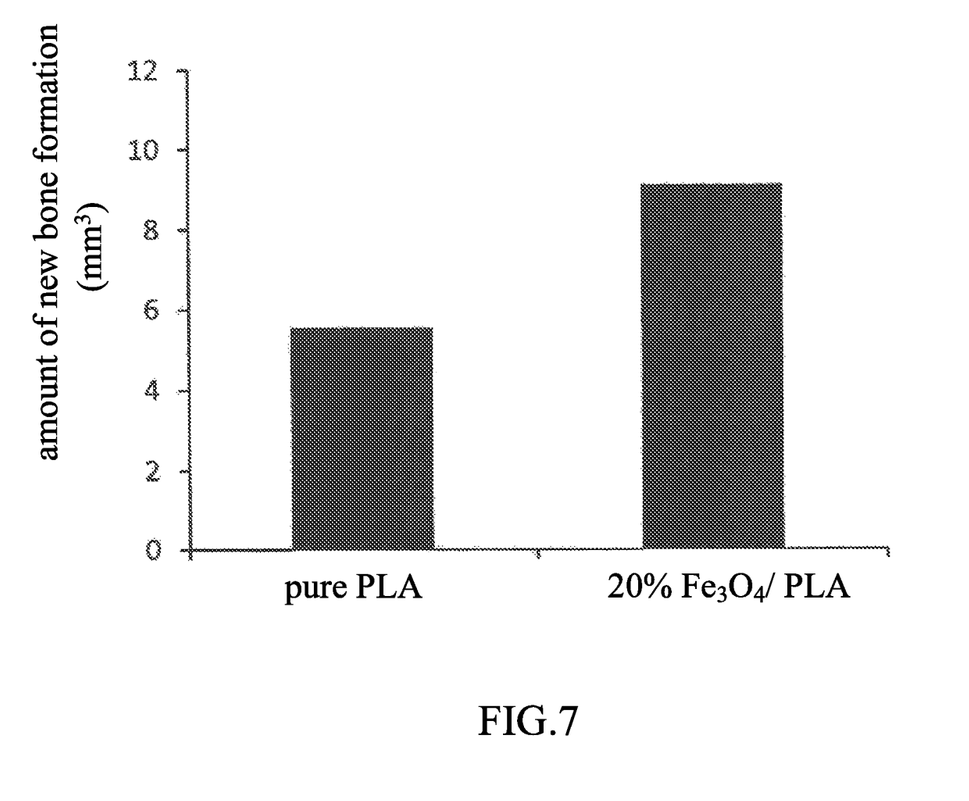
FIG. 7 is a result of a Micro-CT based quantitative analysis, which shows a greater amount of new bone formation around implanted X-ray detectable bioabsorbable bone screw of the present invention compared to the amount of new bone formation around implanted conventional bone screws.

As shown in FIG. 6a, the bone screw made of pure PLA in bone is radiopaque when being exposed to X-ray radiation. As shown in FIG. 6b, the bone screw of the present invention is clearly shown in the bone when being exposed to X-ray radiation. It is thus indicated that the bone screw of the present invention is radiographable under X-ray exposure. As shown in FIG. 7, a result of a Micro-CT based quantitative analysis shows a greater amount of new bone around the implanted X-ray detectable and bioabsorbable bone screw prepared according to the above-mentioned preparation examples compared with the amount of new bone around an implanted conventional bone screw.

According to the above examination result, the bioabsorbable bone screw containing PLA and iron oxide nanoparticles of the present invention is radiographable, and thus can be used for radiographic inspection. Therefore, the bioabsorbable bone screw containing PLA and iron oxide nanoparticles of the present invention can be applied to orthopedics, neurosurgery and plastic surgery to improve the positioning of the implanted bone screw and to achieve the effect of accelerating bone healing. However, the present invention is not limited to the above mentioned advantages.

The above description should be considered as only the preferred embodiments of the present invention, and the scope of the embodiment of present invention is not limited thereto. Various equivalents and modifications without departing from the appended claims and the description of present invention are included in the scope of the present invention.

What is claimed is:

1. An X-ray detectable bioabsorbable bone screw, which is radiographable under X-ray exposure, comprising:
    a screw member having a cylindrical shape; and
    a cap member provided on an end of the screw member and being extended outwardly from the screw member,
    wherein the cap member and the screw member are formed integrally, and the cap member and the screw member are made of polylactic acid, iron oxide nanoparticles, and a bioabsorbable material, the bioabsorbable material is selected from a group consisting of hydroxyapatite, β-tricalcium phosphate, and calcium polyphosphate.

2. The X-ray detectable bioabsorbable bone screw as claimed in claim 1, wherein the cap member and the screw member contain 0.5 to 40 weight percent of iron oxide nanoparticles.

3. The X-ray detectable bioabsorbable bone screw as claimed in claim 1, wherein the cap member and the screw member are manufactured by an injection molding process or a 3D printing process.

4. The X-ray detectable bioabsorbable bone screw as claimed in claim 1, wherein a length extending in an axial direction of the x-ray detectable bioabsorbable bone screw is 16 mm and a diameter of the screw member is 3.1 mm.

5. The X-ray detectable bioabsorbable bone screw as claimed in claim 1, wherein the X-ray detectable bioabsorbable bone screw is biocompatible with an animal cell and is biodegradable by the animal cell.

6. The X-ray detectable bioabsorbable bone screw as claimed in claim 1, wherein the X-ray detectable bioabsorbable bone screw is manufactured by an injection molding process.

7. The X-ray detectable bioabsorbable bone screw as claimed in claim 1, wherein the X-ray detectable bioabsorbable bone screw is manufactured by a die casting process.

8. The X-ray detectable bioabsorbable bone screw as claimed in claim 1, wherein the X-ray detectable bioabsorbable bone screw is manufactured by a 3D printing process.

* * * * *